(12) United States Patent
Ortiz et al.

(10) Patent No.: US 8,715,294 B2
(45) Date of Patent: May 6, 2014

(54) GASTRIC INSTRUMENT SLEEVE TO PREVENT CROSS CONTAMINATION OF STOMACH CONTENT AND PROVIDE FIXATION AND REPEATABLE PATH

(75) Inventors: Mark S. Ortiz, Milford, OH (US); William J. Kraimer, Mason, OH (US); David B. Griffith, Cincinnati, OH (US); Lynetta J. Freeman, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1745 days.

(21) Appl. No.: 11/197,783

(22) Filed: Aug. 5, 2005

(65) Prior Publication Data
US 2007/0043380 A1    Feb. 22, 2007

(51) Int. Cl.
*A61F 11/00*    (2006.01)

(52) U.S. Cl.
USPC ........................................................ 606/108

(58) Field of Classification Search
USPC .......... 606/108, 213; 600/113, 114, 125, 141, 600/184
See application file for complete search history.

(56) References Cited

U.S. PATENT DOCUMENTS

| | | | |
|---|---|---|---|
| 5,080,663 A | 1/1992 | Mills et al. | |
| 5,376,101 A | 12/1994 | Green et al. | |
| 5,437,681 A | 8/1995 | Meade et al. | |
| 5,462,558 A | 10/1995 | Kolesa et al. | |
| 5,514,159 A | 5/1996 | Matula et al. | |
| 5,540,705 A | 7/1996 | Meade et al. | |
| 5,571,119 A | 11/1996 | Atala | |
| 5,709,693 A | 1/1998 | Taylor | |
| 5,713,910 A | 2/1998 | Gordon et al. | |
| 5,800,414 A * | 9/1998 | Cazal | 604/523 |
| 5,814,071 A | 9/1998 | McDevitt et al. | |
| 5,823,956 A | 10/1998 | Roth et al. | |
| 5,855,614 A | 1/1999 | Stevens et al. | |
| 6,036,694 A | 3/2000 | Goble et al. | |
| 6,059,816 A * | 5/2000 | Moenning | 606/213 |
| 6,066,090 A * | 5/2000 | Yoon | 600/113 |
| 6,179,776 B1 * | 1/2001 | Adams et al. | 600/121 |
| 6,190,349 B1 * | 2/2001 | Ash et al. | 604/43 |
| 6,234,958 B1 | 5/2001 | Snoke et al. | |
| 6,346,111 B1 | 2/2002 | Gordon et al. | |
| 6,443,962 B1 | 9/2002 | Gaber | |

(Continued)

FOREIGN PATENT DOCUMENTS

| | | |
|---|---|---|
| EP | 1545336 | 6/2005 |
| EP | 1569709 | 9/2005 |

(Continued)

*Primary Examiner* — Thomas McEvoy
(74) *Attorney, Agent, or Firm* — Welsh Flaxman & Gitler LLC

(57) ABSTRACT

A transgastric instrument provides a sterile and repeatable pathway to and through a gastric wall for the purpose of facilitating endoscopic transgastric procedures. The instrument includes at least one guide tube having a proximal end and a distal end, the distal end being shaped and dimensioned for positioning adjacent a desired location along the gastric wall. The instrument also includes a fixation mechanism at the distal end of the guide tube for selectively securing the distal end of the guide tube at a desired location along the gastric wall. An otomy creation device circumferentially smaller than the guide tube extends through the guide tube, the otomy creation device including a distal end shaped and dimensioned for cutting and dilating the gastric wall.

14 Claims, 3 Drawing Sheets

(56) References Cited

U.S. PATENT DOCUMENTS

| | | |
|---|---|---|
| 6,454,778 B2 | 9/2002 | Kortenbach |
| 6,494,888 B1 | 12/2002 | Laufer et al. |
| 6,506,196 B1 | 1/2003 | Laufer |
| 6,558,400 B2 | 5/2003 | Deem et al. |
| 6,572,629 B2 | 6/2003 | Kalloo et al. |
| 6,632,237 B2 * | 10/2003 | Ben-David et al. ............ 606/213 |
| 6,656,194 B1 | 12/2003 | Gannoe et al. |
| 6,663,639 B1 | 12/2003 | Laufer et al. |
| 6,706,033 B1 * | 3/2004 | Martinez et al. ............... 604/523 |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,773,440 B2 | 8/2004 | Gannoe et al. |
| 6,835,200 B2 | 12/2004 | Laufer et al. |
| 6,908,427 B2 | 6/2005 | Fleener et al. |
| 6,923,819 B2 | 8/2005 | Meade et al. |
| 7,029,435 B2 * | 4/2006 | Nakao ............................ 600/153 |
| 2001/0049497 A1 | 12/2001 | Kalloo et al. |
| 2002/0058884 A1 * | 5/2002 | Burbank et al. ................ 600/564 |
| 2002/0107530 A1 | 8/2002 | Sauer et al. |
| 2002/0111534 A1 | 8/2002 | Suzuki et al. |
| 2003/0083674 A1 | 5/2003 | Gibbens, III |
| 2003/0164304 A1 | 9/2003 | Imran et al. |
| 2003/0171760 A1 | 9/2003 | Gambale |
| 2003/0181924 A1 | 9/2003 | Yamamoto et al. |
| 2003/0229296 A1 | 12/2003 | Ishikawa et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0127913 A1 | 7/2004 | Voss |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0243195 A1 | 12/2004 | Imran et al. |
| 2004/0260344 A1 | 12/2004 | Lyons et al. |
| 2005/0015101 A1 | 1/2005 | Gibbens, III et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0101837 A1 | 5/2005 | Kalloo et al. |
| 2005/0143674 A1 | 6/2005 | Burbank et al. |
| 2005/0148818 A1 | 7/2005 | Mesallum |

FOREIGN PATENT DOCUMENTS

| | | |
|---|---|---|
| WO | WO00/61012 | 10/2000 |
| WO | WO01/10312 | 2/2001 |
| WO | WO01/66001 | 9/2001 |
| WO | WO02/35980 | 5/2002 |
| WO | WO 02/054958 | 7/2002 |
| WO | WO02/085225 | 10/2002 |
| WO | WO2005/053511 | 6/2005 |

* cited by examiner

US 8,715,294 B2

GASTRIC INSTRUMENT SLEEVE TO PREVENT CROSS CONTAMINATION OF STOMACH CONTENT AND PROVIDE FIXATION AND REPEATABLE PATH

BACKGROUND OF THE INVENTION

1. Field of the Invention

The present invention relates to an apparatus for facilitating transgastric surgery. More particularly, the invention relates to a procedure and apparatus for the insertion and placement of a guide tube used in providing a sterile and repeatable pathway for the passage of endoscopic instruments to and through the gastric wall.

2. Description of the Prior Art

Endoscopic procedures have been rapidly developing over the past decade. These procedures often allow for the performance of surgical procedures with minimal trauma, when compared to prior techniques requiring large external openings to expose the internal organs or tissue requiring repair.

In addition to the many areas in which endoscopic procedures have found use, endoscopic procedures have recently been developed for surgical procedures relating to the stomach. Among the endoscopic procedures relating to the stomach are transgastric procedures in which the exterior surface of the stomach is accessed via the esophagus.

However, the passage of endoscopic instruments through the esophagus, into the stomach and through an otomy formed in the gastric wall is replete with complications. For example, otomy creation is difficult and abrasions, tears, from the endoscope rubbing against the esophagus may cause trauma. In addition, the gastric contents may contaminate the peritoneum. The creation of a repeatable path for endoscopic instruments is also difficult and fixation of endoscopic instruments is problematic. Finally, the need occasionally arises for blind insertion of instruments endoscopically. In such cases, the risk of trauma to the esophagus or of inserting the instrument down the trachea is very high.

As such, a need exists for an apparatus and method facilitating transgastric procedures. The present invention provides such a method and apparatus employing a guide tube for the creation of a sterile barrier as an endoscope is passed from the patients' mouth to the peritoneum.

SUMMARY OF THE INVENTION

It is, therefore, an object of the present invention to provide a transgastric instrument providing a sterile and repeatable pathway to and through a gastric wall for the purpose of facilitating endoscopic transgastric procedures. The instrument includes at least one guide tube having a proximal end and a distal end, the distal end being shaped and dimensioned for positioning adjacent a desired location along the gastric wall. The instrument also includes a fixation mechanism at the distal end of the guide tube for selectively securing the distal end of the guide tube at a desired location along the gastric wall. An otomy creation device circumferentially smaller than the guide tube extends through the guide tube, the otomy creation device including a distal end shaped and dimensioned for cutting and dilating the gastric wall.

It is also an object of the present invention to provide a transgastric instrument wherein the otomy creation device is an inner tube designed to cut through the gastric wall.

It is another object of the present invention to provide a transgastric instrument wherein the inner tube is positioned within the guide tube and the inner tube includes a distal end shaped and dimensioned to penetrate the gastric wall.

It is a further object of the present invention to provide a transgastric instrument wherein the distal end of the inner tube includes a bevel cut, sharpened tip which appears as an oval in a front view.

It is also another object of the present invention to provide a transgastric instrument wherein the distal end of the inner tube includes a bevel cut with a tip which comes to a sharp tip at its most distal point.

It is still another object of the present invention to provide a transgastric instrument wherein the distal end of the inner tube includes a hot wire.

It is yet another object of the present invention to provide a transgastric instrument wherein the fixation mechanism is composed of a plurality of shape memory rods.

It is also an object of the present invention to provide a transgastric instrument wherein the rods curl as they are distally moved into the gastric wall to create a fixation point within the gastric wall.

It is a further object of the present invention to provide a transgastric instrument wherein the rods extend to a proximal end of the guide tube where they are manually actuated.

It is also a further object of the present invention to provide a transgastric instrument wherein the fixation mechanism is composed of opposed circumferential balloons secured at the distal end of the guide tube.

It is also another object of the present invention to provide a transgastric instrument wherein the fixation mechanism includes a distal fixation arm and a proximal fixation arm.

It is a further object of the present invention to provide a transgastric instrument wherein the distal fixation arm selectively pivots from a wall of the guide tube.

It is still a further object of the present invention to provide a transgastric instrument wherein the distal fixation arm is an elongated substantially rigid rod extending along the length of the guide tube.

It is yet a further object of the present invention to provide a transgastric instrument wherein the distal fixation arm includes an outwardly oriented protrusion formed at a distal end of the distal fixation arm, and the protrusion is shaped and dimensioned for engaging an exterior surface of the gastric wall upon deployment.

It is also an object of the present invention to provide a transgastric instrument wherein the proximal fixation arm selectively pivots from a wall of the guide tube.

It is also another object of the present invention to provide a transgastric instrument wherein the proximal fixation arm is an elongated substantially rigid rod extending along the length of the guide tube.

It is another object of the present invention to provide a transgastric instrument wherein the proximal fixation arm includes an outwardly oriented protrusion formed at a distal end of the proximal fixation arm, and the protrusion is shaped and dimensioned for engaging an interior surface of the gastric wall upon deployment.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
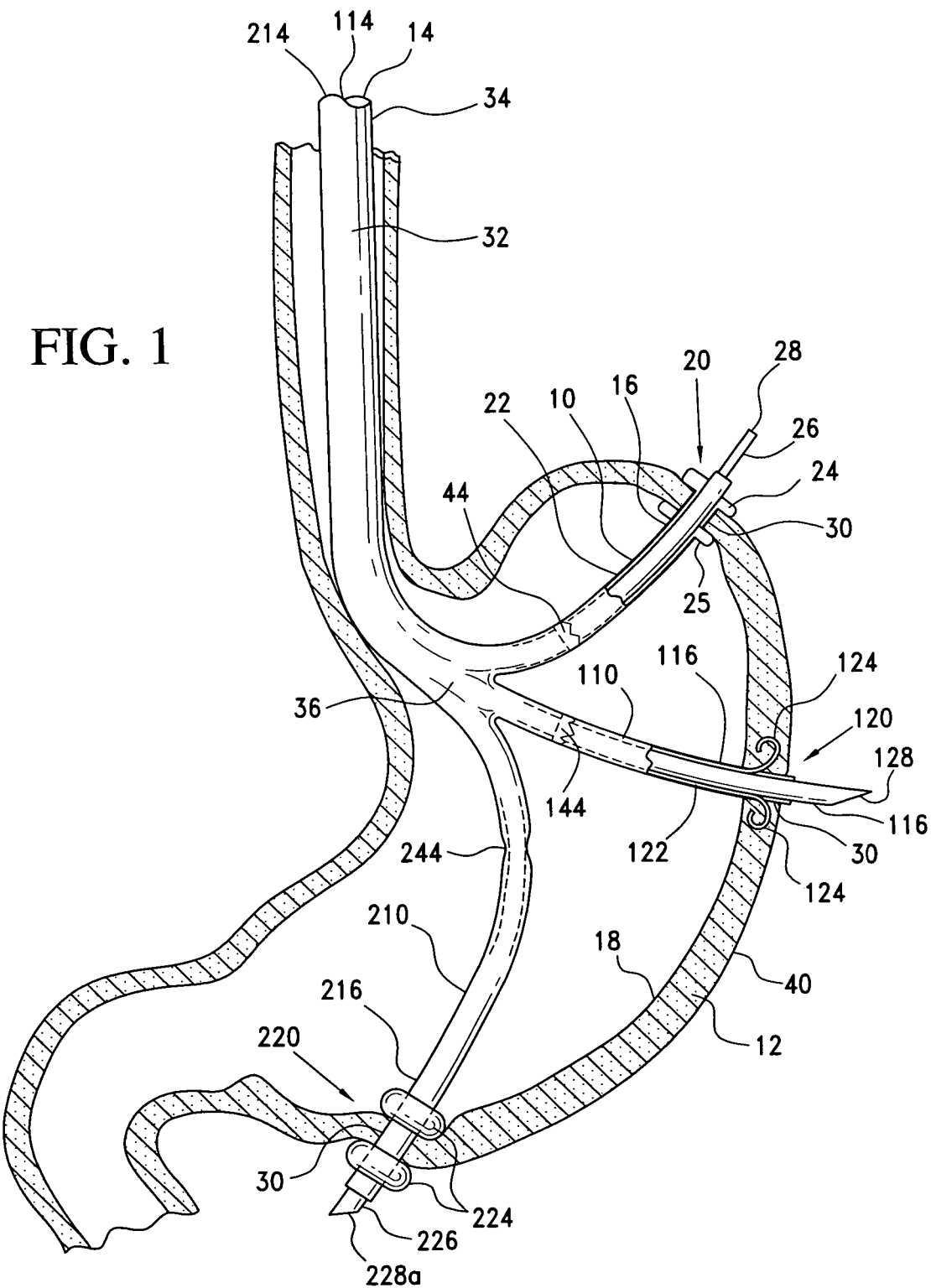
FIG. 1 is a cross-sectional view of the stomach with the present gastric instrument sleeve in use.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures and the embodiments presented herein, a procedure and apparatus for the insertion and placement of a guide tube(s) 10, 110, 210 is disclosed. The guide tubes 10, 110, 210 are used in providing a sterile and repeatable pathway to and through the gastric wall 12 for the purpose of facilitating endoscopic transgastric procedures. The guide tube(s) 10, 110, 210 includes a proximal end 14, 114, 214 and a distal end 16, 116, 216. The distal end 16, 116, 216 is positioned adjacent a desired location along the internal surface 18 of the gastric wall 12 in a manner described below in greater detail. Thereafter, various fixation mechanisms 20, 120, 220 are employed in securing the distal end 16, 116, 216 of the guide tube 10, 110, 210 at the desired location along the gastric wall 12.

As will be discussed below in greater detail, the fixation mechanism 20, 120, 220 may take a variety of forms. The figures presented herein disclose an apparatus employing different fixation mechanisms within the same apparatus. However, the apparatus used in practice may be constructed with any combination of fixation mechanisms without departing from the spirit of the present invention.

For example, and as will be discussed below in greater detail, the guide tube 10, 110 may be formed with a plurality of radial extruded pathways 22, 122 containing small diameter rods 24, 124, or splines, that are advanced distally out of the guide tube 10, 110 and inserted into the gastric wall 12 or other tissue in a controlled depth manner. The rods 24, 124 can come out of the guide tube 10, 110 in a variety of configurations including a shape memory alloy rod 124 which is straight in the retracted state and when advanced distally curls into a loop while penetrating through the mucosal layer of the stomach with its sharpened point (see guide tube 110). It is further contemplated the rod 24 may be constructed to pivot once it has penetrated the gastric wall 12 in a manner preventing the rod 24 from coming back through the gastric wall 12. While some rod designs will advance and penetrate into the mucosal layer, and others will puncture through the gastric wall, the objective of the rod-based coupling design is to provide fixation and to provide counter-traction when inserting a dilating trocar inner tube through the gastric wall.

As will be discussed below in greater detail, fixation may also be achieved through the utilization of opposed circumferential balloons 224 shaped and dimensioned to trap the gastric wall 12 therebetween in a manner securing the distal end 216 of the guide tube 210 to the gastric wall 12. In addition, and as those skilled in the art will certainly appreciate, other fixation techniques may also be used without departing from the spirit of the present invention.

As briefly mentioned above, the present apparatus also includes an otomy creation device 26, 126, 226, for example, an inner tube designed to cut through the gastric wall 12 for otomy creation. As with the disclosed fixation mechanisms, the figures presented herein disclose a preferred apparatus, although those skilled in the art will appreciate any combination of otomy reaction devices within the spirit of the present invention. Regardless of the chosen embodiment, the inner tube 26, 126, 226 is circumferentially smaller than the guide tube 10, 110, 210 and includes a proximal end and a distal end. The distal end is designed for penetrating the gastric wall 12 and may be provided with a variety of constructions. For example, it is contemplated the distal end may have a bevel cut 28 with a modified tip which comes to a sharp tip at its most distal point, a bevel cut, sharpened tip 128 which appears as an oval in a front view, a tip construction which uses a hot wire 228 to cut the tissue (see FIG. 4) or a veress needle 222a embodiment (see FIG. 1).

In addition to cutting through the gastric wall 12, the otomy creation device 26, 126, 226 dilates the otomy 30 as it passes through the gastric wall 12. This creates a sterile pathway to pass an endoscopic instrument through the gastric wall 12 to the peritoneum without contamination from gastric contents when used in conjunction with the guide tube 10, 110, 210.

Figure 11:
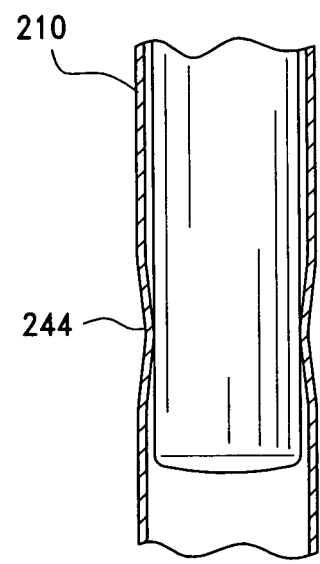
Figure 12:
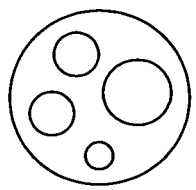
FIGS. 12, 13 and 14 show various lumen constructions that may be employed in accordance with the present invention.
Figure 13:
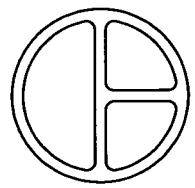
Figure 14:
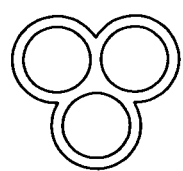

Referring to FIGS. 1 to 14, a preferred embodiment of the present invention is disclosed. The present transgastric instrument includes a tubular main body 32 having a plurality of lumens, that is, guide tubes 10, 110, 210, extending therethrough. Referring to FIGS. 12 to 14, those skilled in the art will appreciate a variety of different lumen shapes and structures may be used within the spirit of the present invention. The guide tubes 10, 110, 210 are ultimately coupled to the gastric wall 12 for the performance of transgastric procedures. In particular, the main body 32 includes a proximal end 34 and a distal end 36. At the proximal end 34 of the main body 32, the plurality of lumens are maintained in a cohesive unit. The lumens, however, ultimately diverge to define a plurality of separate guide tubes 10, 110, 210 as the main body 32 extends toward its distal end 36. The guide tubes 10, 110, 210 ultimately are used in providing a sterile and repeatable pathway to the transgastric sites. Although three guide tubes are disclosed in accordance with a preferred embodiment of the present invention, the transgastric instrument may be constructed with fewer or greater guide tubes if desired.

Each of the guide tubes 10, 110, 210 which diverge from the primary main body 32, are adapted for coupling along the gastric wall 12 such that a penetrating obturator, or other gastrotomy creation device, may extend therethrough and cut through the gastric wall 12 for the purpose of permitting transgastric procedures to take place. With this in mind, each of the guide tubes 10, 110, 210 includes a distal end 16, 116, 216 at which a fixation mechanism 20, 120, 220 is provided.

The fixation mechanism 20, 120, 220 is provided for securing the distal end 16, 116, 216 of the respective guide tubes 10, 110, 210 to the gastric wall 12 for the creation of a seal and a repeatable pathway for performing transgastric procedures.

Figure 2:
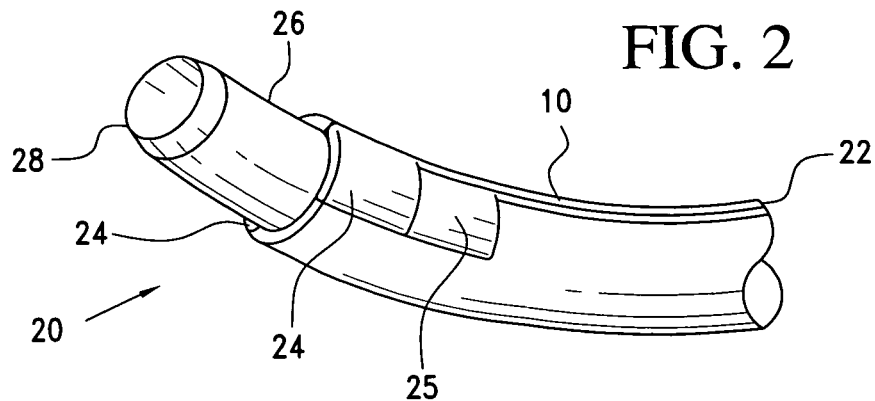
FIG. 2 is a detailed perspective view of a first embodiment of a fixation mechanism in accordance with the present invention.
Figure 3:
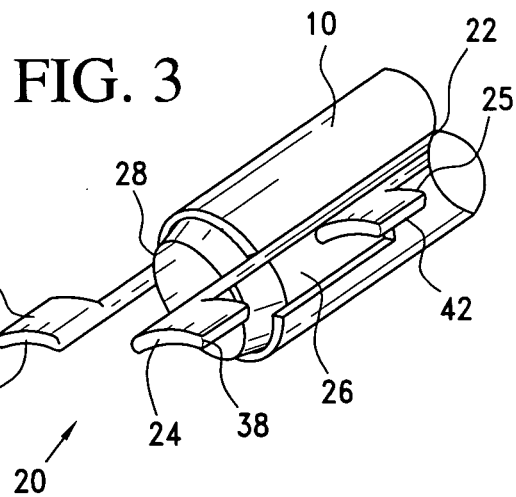
FIG. 3 is a detailed view of the embodiment shown in FIG. 2 with the fixation arms extended.

Referring to the fixation mechanism 20 disclosed with reference to FIGS. 1, 2 and 3, the fixation mechanism 20 includes distal and proximal fixation arms 24, 25 adapted to pivot slightly from the wall of the guide tube 10 as they are positioned on opposite sides of the gastric wall for securing the distal end 16 of the guide tube 10 at a predetermined location along the gastric wall 12. The distal and proximal fixation arms 24, 25 also move longitudinally relative to the guide tube 10. In accordance with a preferred embodiment, the fixation arms 24, 25 extend to the handle (not shown) where they are manually actuated.

More particular, each of the distal fixation arms 24 (two are provided in accordance with a preferred embodiment) is an elongated substantially rigid rod extending along the length of the guide tube 10 for actuation from the proximal end 34 of the main body 32. An outwardly oriented protrusion 38 is formed at the distal end of the distal fixation arm 24 and is shaped and dimensioned for engaging the exterior surface 40 of the gastric wall 12 upon deployment.

The distal fixation members 24 are deployed by slightly rotating them to bring the protrusion 38 out of alignment with the exterior surface of the guide tube 10 and unlocking the distal fixation member 24 for further distal movement. Thereafter, the distal fixation member 24 is pushed distally through the gastric wall 12 until the protrusion 38 is beyond the exterior surface 40 of the gastric wall 12. At this point, the protrusion 38 is rotated out of alignment with its passageway and is drawn proximally, trapping the gastric wall 12 between the protrusion 38 and the protrusion 42 of the proximal fixation arm 25 (two are provided in accordance with a preferred embodiment of the present invention), which is similarly rotated outwardly from the guide tube 10 wall.

Figure 5:
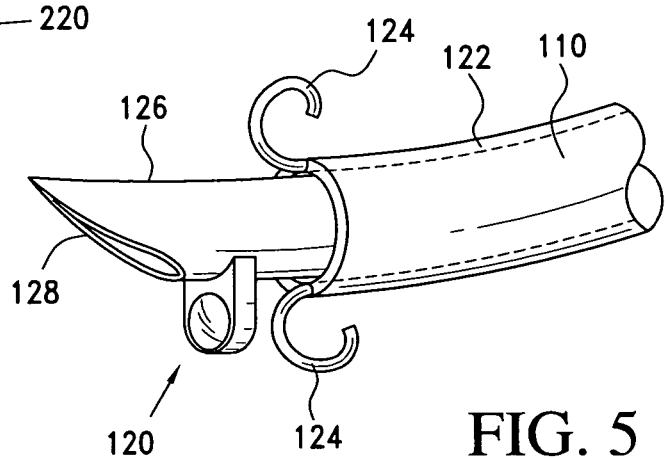
FIG. 5 is yet another embodiment of the fixation mechanism utilized in conjunction with the present gastric instrument sleeve.
Figure 6:
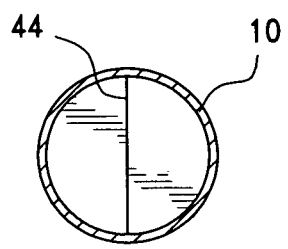
FIGS. 6, 7 and 8 disclose a seal mechanism for use in conjunction with the present gastric instrument sleeve.
Figure 7:
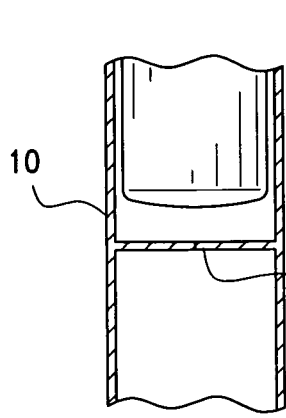
Figure 8:
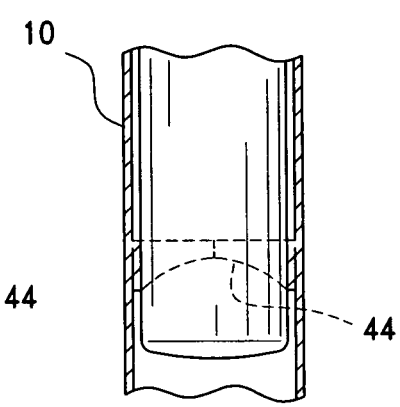

With reference to FIGS. 1 and 5, the fixation mechanism 120 may take the form of a plurality of shape memory (for example, Nitinol) rods 124 embedded within the pathways 122 formed in the wall of the guide tube 110 for selective retrieval when fixation is required. The rods 124 curl as they are distally moved into the gastric wall 12 and loop within the gastric wall 12 to create a fixation point within the gastric wall 12. In accordance with a preferred embodiment, the rods 124 extend to the handle (not shown) where they are manually advanced.

Figure 4:
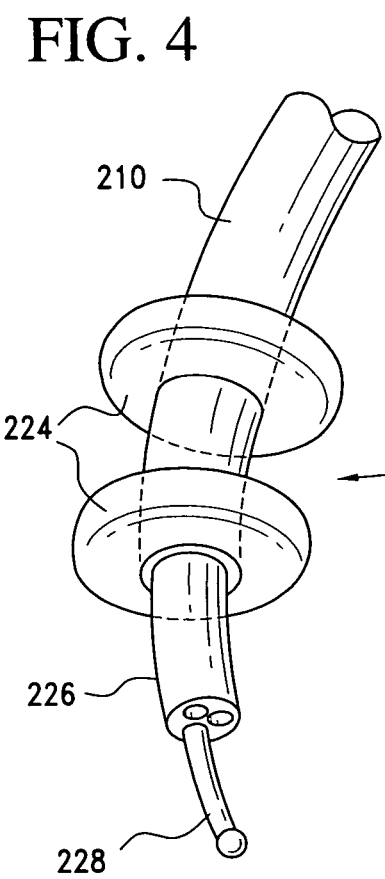
FIG. 4 is a detailed perspective view of the fixation mechanism employed in accordance with a second embodiment of the present guide tube.

An alternate embodiment is disclosed with reference to FIGS. 1 and 4. In accordance with this alternate embodiment, opposed circumferential balloons 224 are secured at the distal end 216 of the guide tube 210. The circumferential balloons 224 are selectively inflated on both sides of the gastric wall 12 to provide for fixation of the guide tube 210 at the gastric wall 12. The balloons 224 are actuated in a conventional manner using fluid supply lumens (not shown) extending along the length of the guide tube 210.

Figure 9:
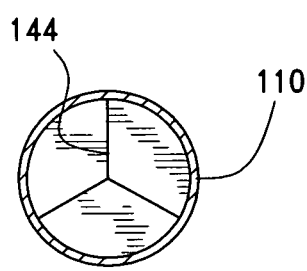
FIG. 9 shows a further embodiment of a seal mechanism that may be utilized in conjunction with the present gastric instrument sleeve.
Figure 10:
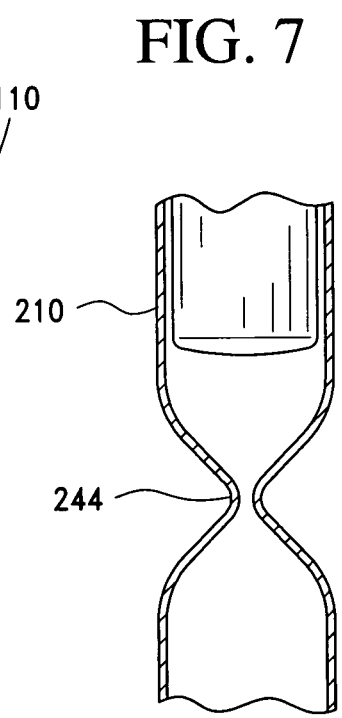
FIGS. 10 and 11 disclose yet another embodiment of a seal mechanism which may be used in conjunction with the present invention.

As with the fixation mechanisms 20, 120, 220, a plurality of seal mechanisms 44, 144, 244 may be employed along the length of the guide tube 10, 110, 210 for preventing insufflation. For example and with reference to FIGS. 6, 7 and 8, a single slit design 44 may be utilized. Similarly, a tri-slit design 144 could be utilized as shown in FIG. 9 or a sphincter sleeve 244 may be utilized as shown in FIGS. 10 and 11. While a variety of seal structures are disclosed in accordance with a preferred embodiment of the present invention, those skilled in the art will appreciate various seal structures could be utilized without departing from the spirit of the present invention. A preferred design employs two overlapping latex or silicone leaves shaped and dimensioned for permitting the passage of an instrument therethrough.

In practice, and in accordance with a preferred embodiment of the present invention, the main body 32 with the plurality of guide tubes 10, 110, 210 depending therefrom is inserted down the esophagus and into the stomach. A gastroscope is then inserted into one of the lumens of the main body 32. The gastroscope is moved down the esophagus and into the stomach of the patient. Once the gastroscope is inserted within the stomach, it is used to determine the proper sites for gastrotomies for each of the guide tubes 10, 110, 210 and for the creation of various fixation points at which the distal ends 16, 116, 216 of the guide tubes 10, 110, 210 will be secured.

In conjunction with the utilization of a gastroscope, a gastrotomy creation device 26, 126, 226 is inserted down one of the other lumens. The gastrotomy creation device may be an RF needle knife, an obturator such as is used in existing endopath devices or a beveled hollow needle. As those skilled in the art will appreciate, a variety of gastrotomy creation devices may be used without departing from the spirit of the present invention. The gastroscope and gastrotomy creation device are utilized to create a gastrotomy.

Once the gastrotomy is created, the gastrotomy creation device 26, 126, 226 is extracted, the distal end 16, 116, 216 of the guide tube 10, 110, 210 is placed at the gastric wall 12 adjacent the created gastrotomy and the fixation mechanism 20, 120, 220 is then deployed. It is also contemplated that the distal end of the guide tube may be affixed to the gastric wall before the gastrotomy is created.

Where the pivoting rod fixation mechanism 20 is used, the proximal fixation arm 25 is deployed first so that the depth of insertion of the guide tube 10 through the gastrotomy may be controlled. Once the proximal fixation arm 25 is deployed, the distal end 16 of the guide tube 10 is pushed through the gastrotomy and the distal fixation arm 24 is deployed such that the guide tube 10 is now fixed to the abdominal wall. At this point, cross contamination of the stomach contents into the peritoneal cavity is prevented.

In accordance with a preferred embodiment, an insufflation seal 44, 144, 244 is employed. As discussed above, and in accordance with a preferred embodiment of the present invention, the insufflation seal may be an elastic band like sphincter valve 244 incorporated in the wall of the guide tube 10, 110, 210. The seal 10, 110, 210 dilates to accommodate instruments that are inserted down the sleeve. This passive seal is normally closed and also seals around the shaft of any device inserted down the tube to thereby maintain insufflation.

The same procedure is repeated for each of the guide tubes that are to be fixed along the gastric wall. As necessary, the gastroscope may be moved to other lumens to provide visualization as necessary. Additionally, it may be desirable for the gastroscope to be moved to the first deployed cannula immediately after deployment so as to visualize gastrotomy creation of the additional cannulas and to ensure safe otomy creation.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A transgatric instrument providing a sterile and repeatable pathway to and through a gastric wall for the purpose of facilitating endoscopic transgastric procedures, comprising:
a tubular main body including a plurality of lumens each defining a guide tube, each of the guide tubes having a proximal end and a distal end, the distal end being shaped and dimensioned for positioning adjacent a desired location along the gastric wall; a first fixation mechanism is provided at the distal end of at least one of the guide tubes for selectively securing the distal end of the guide tube at a desired location along the gastric wall and a second fixation mechanism is provided at the distal end of at least one of the guide tubes for selectively securing the distal end of the guide tube at a desired location along the gastric wall;

an otomy creation device, circumferentially smaller than the respective guide tubes, extends through the respective guide tubes, the otomy creation device includes a distal end shaped and dimensioned for cutting and dilating the gastric wall;

the first fixation mechanism is composed of a plurality of shape memory rods embedded in pathways formed in a wall of the guide tube; and wherein the second fixation mechanism includes a pivotally and longitudinally moveable distal fixation arm having an outwardly oriented protrusion selectively moved from an aligned orientation to and out of alignment orientation and a pivotally moveable proximal fixation arm having an outwardly oriented protrusion selectively moved from an aligned orientation to and out of alignment orientation.

2. The transgastric instrument according to claim 1, wherein the distal fixation arm selectively pivots from a wall of the guide tube.

3. The transgastric instrument according to claim 1, wherein the distal fixation arm is an elongated substantially rigid rod extending along the length of the guide tube for actuation thereof from a proximal end of the main body.

4. The transgastric instrument according to claim 3, wherein the outwardly oriented protrusion of the distal fixation arm is shaped and dimensioned for engaging an exterior surface of the gastric wall upon deployment.

5. The transgastric instrument according to claim 4, wherein the proximal fixation arm selectively pivots from a wall of the guide tube.

6. The transgastric instrument according to claim 5, wherein the proximal fixation arm is an elongated substantially rigid rod extending along the length of the guide tube for actuation thereof from a proximal end of the main body.

7. The transgastric instrument according to claim 6, wherein an outwardly oriented protrusion of the proximal fixation arm is shaped and dimensioned for engaging an interior surface of the gastric wall upon deployment.

8. A transgastric instrument providing a sterile and repeatable pathway to and through a gastric wall for the purpose of facilitating endoscopic transgastric procedures, comprising:

a tubular main body including a plurality of lumens each defining a guide tube, each of the guide tubes having a proximal end and a distal end, the distal end being shaped and dimensioned for positioning adjacent a desired location along the gastric wall; a first fixation mechanism is provided at the distal end of at least one of the guide tubes for selectively securing the distal end of the guide tube at a desired location along the gastric wall and a second fixation mechanism is provided at the distal end of at least one of the guide tubes for selectively securing the distal end of the guide tube at a desired location along the gastric wall;

an otomy creation device, circumferentially smaller than the respective guide tubes, extends through the respective guide tubes, the otomy creation device includes a distal end shaped and dimensioned for cutting and dilating the gastric wall;

the first fixation mechanism is composed of opposed circumferential balloons secured at the distal end of the guide tube; and wherein the second fixation mechanism includes a pivotally and longitudinally moveable distal fixation arm having an outwardly oriented protrusion selectively moved from an aligned orientation to and out of alignment orientation and a pivotally moveable proximal fixation arm having an outwardly oriented protrusion selectively moved from an aligned orientation to and out of alignment orientation.

9. The transgastric instrument according to claim 8, wherein the distal fixation arm selectively pivots from a wall of the guide tube.

10. The transgastric instrument according to claim 8, wherein the distal fixation arm is an elongated substantially rigid rod extending along the length of the guide tube for actuation thereof from a proximal end of the main body.

11. The transgastric instrument according to claim 10, wherein the outwardly oriented protrusion of the distal fixation arm is shaped and dimensioned for engaging an exterior surface of the gastric wall upon deployment.

12. The transgastric instrument according to claim 11, wherein the proximal fixation arm selectively pivots from a wall of the guide tube.

13. The transgastric instrument according to claim 12, wherein the proximal fixation arm is an elongated substantially rigid rod extending along the length of the guide tube for actuation thereof from a proximal end of the main body.

14. The transgastric instrument according to claim 13, wherein an outwardly oriented protrusion of the proximal fixation arm is shaped and dimensioned for engaging an interior surface of the gastric wall upon deployment.

\* \* \* \* \*